US011878032B2

(12) United States Patent
Djellouli et al.

(10) Patent No.: US 11,878,032 B2
(45) Date of Patent: Jan. 23, 2024

(54) AQUEOUS SALINE COMPOSITION, PROCESS FOR THE PRODUCTION OF SAME, AND USE OF SAME

(71) Applicants: Saïd Djellouli, Paris (FR); Andrea Fox, Paris (FR)

(72) Inventors: Saïd Djellouli, Paris (FR); Andrea Fox, Paris (FR)

(*) Notice: Subject to any disclaimer, the term of this patent is extended or adjusted under 35 U.S.C. 154(b) by 147 days.

(21) Appl. No.: 17/268,919

(22) PCT Filed: Nov. 8, 2019

(86) PCT No.: PCT/EP2019/080694
§ 371 (c)(1),
(2) Date: Feb. 16, 2021

(87) PCT Pub. No.: WO2020/099264
PCT Pub. Date: May 22, 2020

(65) Prior Publication Data
US 2021/0299171 A1    Sep. 30, 2021

(30) Foreign Application Priority Data

Nov. 13, 2018 (FR) .................................. 1871509

(51) Int. Cl.
| | | |
|---|---|---|
| *A61K 35/08* | (2015.01) |
| *A61K 9/00* | (2006.01) |
| *A61K 9/08* | (2006.01) |
| *A61K 47/26* | (2006.01) |
| *A61K 33/04* | (2006.01) |
| *A61K 33/06* | (2006.01) |
| *A61K 33/14* | (2006.01) |

(52) U.S. Cl.
CPC ............ *A61K 35/08* (2013.01); *A61K 9/0043* (2013.01); *A61K 9/08* (2013.01); *A61K 33/04* (2013.01); *A61K 33/06* (2013.01); *A61K 33/14* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 4,307,097 A * | 12/1981 | Kanno ................... | A61P 43/00 514/255.03 |
| 6,258,372 B1 | 7/2001 | Jones | |
| 2013/0156868 A1 | 6/2013 | Schierstedt | |
| 2015/0104527 A1 | 4/2015 | Andro | |

FOREIGN PATENT DOCUMENTS

| | | | | |
|---|---|---|---|---|
| CN | 1775222 | A | 5/2006 | |
| CN | 101559046 | A | 10/2009 | |
| CN | 105326786 | A | 2/2016 | |
| DE | 20201300748 | U1 * | 2/2013 | |
| EA | 025945 | B1 | 2/2017 | |
| EP | 3369429 | A1 | 9/2018 | |
| WO | WO-9808500 | A1 * | 3/1998 | ........... A61K 31/195 |
| WO | WO9808500 | A1 | 3/1998 | |
| WO | WO-2006102438 | A2 * | 9/2006 | ............. A61K 33/00 |
| WO | 2008/037938 | A1 | 4/2008 | |
| WO | WO2008037938 | A1 | 4/2008 | |
| WO | 2016/155992 | A1 | 10/2016 | |

OTHER PUBLICATIONS

Nasal spray development: formulation and device consideration-Renaissance, accessed online Feb. 17, 2023. (Year: 2023).*
The First Examination Opinion dated Jul. 6, 2022 from China National Intellectual Property Administration for Application No. 201980058305.9.
International Search Report dated Feb. 7, 2020 for related International Patent Application No. PCT/EP2019/080694.
The Official Action for Russian Patent Application No. 2021103673, dated Jul. 21, 2021.
The Second Examination Opinion for Chinese Patent Application No. 201980058305.9, dated Jan. 13, 2023.
Bryne, Rober Howard, et al., "seawater," Encyclopedia Britannica, saved from Mar. 19, 2018.
The Dismissing Decision dated Jun. 14, 2023 from China National Intellectual Property Administration for Application No. 201980058305.9.
The Office Action for Mexican Patent Application No. MX/a/2021/001942, dated Jul. 21, 2023.
The Office Action for Canadian Patent Application No. 3,109,555, dated Aug. 16, 2023. X.

* cited by examiner

*Primary Examiner* — Melissa S Mercier

(57) ABSTRACT

An aqueous saline composition comprising an organic film-protective and/or hyperosmotic compound, the method for obtaining the same, the use thereof as a drug, for example in the form of a spray, for prophylaxis, prevention or adjuvant treatment of ear, nose and throat-(ENT) conditions.

18 Claims, No Drawings

AQUEOUS SALINE COMPOSITION, PROCESS FOR THE PRODUCTION OF SAME, AND USE OF SAME

The object of the present invention relates to an aqueous saline composition, the process to obtain it, its use as a drug, for example in spray device form for the prevention or adjuvant treatment of ear, nose and throat (ENT) conditions.

The nasal cavities act as a filter that helps protect against ear, nose and throat (ENT) conditions such as sinusitis, rhinitis, etc. However, various salt-water-based compositions, such as seawater, are known for washing the nasal cavity, in particular in the context of such pathologies.

For example, such seawater-based compositions are generally indicated as they are isotonic. These compositions can be obtained by mixing seawater with purified water, or by extracting certain ions (sodium, potassium, chloride, etc.— for example by electrodialysis). These mixtures can be subjected to sterilisation procedures, such as filtration (preferentially) or UV radiation before packaging. The compositions obtained can also be radio-sterilised (beta or gamma radiation). Products are packaged as aerosol spray devices or mechanical spray devices. Document FR 2 299 041 or WO 2008/037,938 relate to such a composition.

In a completely separate therapeutic field, document EP 3,369,429 describes a saline composition comprising an oxytocin and a carboxyvinil polymer, and an osmolality lower than that of physiological serum, that is to say less than 286 mosmol/kg.

In a completely distinct therapeutic field, document WO 98/08500 describes an aqueous saline composition containing arginine-L, for correcting cerebral ischemias and hypoxia in the case of combinations of brain trauma (TBI) and hemorrhages.

The present invention aims to improve the effectiveness of known seawater-based compositions.

SUMMARY OF THE INVENTION

The object of the present invention relates to an aqueous saline composition comprising an organic film-protective and/or hyper-osmotic compound characterized in that it comprises a polyol derived from a saccharide compound, the saccharide compound in question, or a mixture thereof and in that the osmolarity of said composition is higher than 1000 mosmol/l at 20° C.

According to an embodiment, the osmolarity of said composition is higher than 1,500 mosmol/l at 20° C.

According to an embodiment, the osmolarity of said composition is less than 2,000 mosmol/l at 20° C.

The object of the present invention also relates to the manufacturing process of an aqueous composition comprising an organic film-protective and/or hyperosmotic compound, comprising a polyol derived from a saccharide compound, the saccharide compound in question, or a mixture thereof, and with an osmolarity higher than 1000 mosmol/l at 20° C., comprising the following steps:
a) microfiltration of seawater;
b) addition of purified water;
c) mixing;
d) while mixing, addition to the solution from step c) of the organic film-protective and/or hyperosmotic compound;
e) recovery of the mixture from step d);
said process being characterised in that the quantity of seawater is higher than or equal to 10% of the total mass of the aqueous composition obtained in step e) and in that the quantity of organic film-protective and/or hyperosmotic compound is higher than or equal to 5% of the total mass of the aqueous composition obtained in step e).

According to one aspect, the quantity of seawater is higher than or equal to 15%, 20%, 30%, 40%, 50%, 60%, 70% or 80% of the total mass of the aqueous composition obtained in step e) and/or the quantity of organic film-protective and/or hyperosmotic compound is higher than or equal to 6%, 7%, 8%, 9%, 10%, 15%, 20%, preferentially 11%, of the total mass of the aqueous composition obtained in step e).

Thus, the object of the present invention relates to a composition obtainable by the manufacturing process described above.

According to one aspect, the composition comprises:
a chloride concentration between 2 and 18 g/kg
a sodium concentration between 1 and 10 g/kg
a sulphate concentration between 0.3 and 2.4 g/kg
a magnesium concentration between 0.1 and 1.2 g/kg
a calcium concentration between 0.04 and 0.4 g/kg
a potassium concentration between 0.04 and 0.4 g/kg
and/or a pH between 4 and 10, preferably between 5 and 9, for example 7.

According to one aspect, the composition is in final dosage forms selected from the group consisting of nasal drops, liquid nasal sprays and nasal washes.

According to one aspect, the polyol derived from a saccharide compound, the saccharide compound in question, or a mixture thereof is selected frommaltitol, mannitol, sorbitol, lactitol, galactitol, erythritol, arabitol, xylitol or ribitol, or a mixture thereof.

Moreover, the object of the present invention relates to a composition such as the one described herein, as a drug exhibiting a therapeutic effect.

According to one aspect, the composition comprises seawater.

More specifically, the object of the present invention relates to a composition such as the one described herein, for its use in the treatment and prevention of ear, nose and throat (ENT) conditions.

Lastly, the object of the present invention relates to a nasal administration device, such as a spray device, characterised in that it comprises a composition according to the present invention.

Definitions

In the context of the present invention, "organic film-protective compound" is understood to be a compound with the property of protecting the biological surface to which said compound is applied. In this case, this compound protects the epithelium of the nasal cavities and improves motile cilia function. This compound comprises at least one "C—H" group, where "C" represents a carbon atom and "H" a hydrogen atom. This compound may notably be a polyol. Preferably, it is a derivative of a saccharide compound. In particular, the compound can be a polysaccharide or a monosaccharide. For instance, the monosaccharide can be a tetrose, pentose or hexose. According to some embodiments, the organic film-protective compound is selected from maltitol, mannitol, sorbitol, lactitol, galactitol, erythritol, arabitol, xylitol and ribitol, preferentially xylitol. This organic film-protective compound can also or alternatively be combined with or replaced by the corresponding saccharide. Particularly, as regards xylitol, it can be combined with or replaced by xylose. The organic film-protective compound can be obtained by synthesis or by extraction of natural product.

In the context of this invention, solution "tonicity" refers to the salt concentration of the solution compared to that of human blood. Thus, "isotonic" denotes a solution with a solute concentration equal to that of blood. "Hypotonic" denotes a solution with a solute concentration less than that of blood. "Hypertonic" denotes a solution with a solute concentration higher than that of blood.

In the context of the present invention, "hyperosmotic compound" is defined as a compound with high osmotic power or a compound resulting from or causing very fast osmosis. Osmosis is a phenomenon involving the diffusion of matter which is evidenced when solvent molecules cross the semi-permeable membrane separating two solutions that have different solute concentrations. Overall solvent transfer is thus from the solution with a lower concentration to the one with a higher concentration until equilibrium is achieved. This compound can be organic, i.e. it can comprise at least one "C—H" group, where "C" represents a carbon atom and "H" a hydrogen atom. This compound may be a polyol, for example. Preferably, it is a compound derived from a saccharide compound. In particular, the saccharide compound can be a polysaccharide or a monosaccharide. For instance, the monosaccharide can be a tetrose, pentose or hexose. Preferably, the organic hyperosmotic compound is selected from maltitol, mannitol, sorbitol, lactitol, galactitol, erythritol, arabitol, xylitol and ribitol, preferentially xylitol. This organic film-protective compound can also or alternatively be combined with or replaced by the corresponding saccharide. Particularly, as regards xylitol, it can be combined with or replaced by xylose. The organic hyperosmotic compound can be obtained by synthesis or by extraction of natural product. To determine whether a compound is hyperosmotic according to the present invention, a test can be performed using an osmometer. For example, osmolarity can be measured using a cryoscopic osmometer, by measuring freezing point, with reference to that of distilled water. There are other known osmometry technologies that can be calibrated to obtain results similar to those of cryoscopic osmometers.

In the context of the present invention, "aqueous saline composition" is understood to mean a composition comprising water and salt. If the aqueous saline composition is preferentially a seawater-based composition, any type of salt with the same properties as the salts found in seawater, once dissolved in water, may be used. "Aqueous saline composition" is preferentially understood to mean a composition comprising water and at least one salt found in seawater. Preferentially, the salt is NaCl. The seawater can also contain other elements, such as sulphate, magnesium, calcium, potassium, copper, iron and zinc.

In the context of the present invention, "osmolality" is understood to be the number of osmoles of solute per kilogram of solvent. In the context of the present invention, "osmolarity" is understood to be the number of osmoles of solute per liter of solution. One osmole is equal to the number of moles of particles that can be osmotically active in a model solution.

DETAILED DESCRIPTION

Manufacturing Process of an Aqueous Composition According to the Invention

The object of the present invention thus relates to the manufacturing process of an aqueous composition as described above.

According to an embodiment, the manufacturing process comprises the following steps:

a) microfiltration of seawater;
b) addition of purified water;
c) mixing;
d) while mixing, addition to the solution from step b) of the organic film-protective and/or hyperosmotic compound;
e) recovery of the mixture from step d).

Preferably, the manufacturing process of an aqueous composition according to the present invention can be characterised in that the quantity of seawater is higher than or equal to 15%, 20%, 30%, 40%, 50%, 60%, 70% or 80% of the total mass of the aqueous composition obtained in step e) and/or in that the quantity of organic film-protective and/or hyperosmotic compound is higher than or equal to 6%, 7%, 8%, 9%, 10%, 15%, 20%, preferentially 11%, of the total mass of the aqueous composition obtained in step e).

In a particular embodiment, the manufacturing process of an aqueous composition according to the present invention can be characterised in that the organic film-protective and/or hyperosmotic compound is a polyol, particularly one derived from a saccharide.

Preferably, the manufacturing process of an aqueous composition according to the present invention can be characterised in that the organic film-protective and/or hyperosmotic compound is a monosaccharide and/or a polyol derived from said monosaccharide, or a mixture thereof.

Preferably, the manufacturing process of an aqueous composition according to the present invention can be characterised in that the organic film-protective and/or hyperosmotic compound is selected from maltitol, mannitol, sorbitol, lactitol, galactitol, erythritol, arabitol, xylitol and ribitol, preferentially xylitol, or a mixture thereof. This/These organic film-protective compound(s) can also or alternatively be combined with or replaced by the corresponding saccharide(s). Particularly, as regards xylitol, it can be combined with or replaced by xylose.

In a particular embodiment, the manufacturing process of an aqueous composition according to the present invention can be characterised in that step a) is performed by filtering seawater through a 0.2 μm filter or through a 0.1 μm sterilising filter.

Composition

The object of the present invention relates to an aqueous saline composition as described above, i.e. one that can be characterised by its osmolarity, for example. A particular embodiment relates to an aqueous saline composition that can be obtained by the aforementioned process. In fact, one of the embodiments according to the present invention relates to the use of seawater, which may include a variety of potentially active chemical species.

Thus, in a particular embodiment, the aqueous composition according to the present invention can be characterised in that said composition comprises:
a chloride concentration between 2 and 18 g/kg
a sodium concentration between 1 and 10 g/kg
a sulphate concentration between 0.3 and 2.4 g/kg
a magnesium concentration between 0.1 and 1.2 g/kg
a calcium concentration between 0.04 and 0.4 g/kg
a potassium concentration between 0.04 and 0.4 g/kg
and/or a pH between 4 and 10, preferably between 5 and 9, for example. 7

The aqueous composition may also include copper. The aqueous composition may also include zinc.

Preferably, the aqueous composition according to the present invention can be characterised in that said composition comprises seawater.

Preferably, the aqueous composition according to the present invention can be characterised in that it can form final dosage forms selected from the group consisting of nasal drops, nasal sprays and nasal washes.

In a particular embodiment, the aqueous composition according to the present invention can be characterised in that the organic film-protective and/or hyperosmotic compound is a polyol, particularly a compound derived from a saccharide compound. For example, it can be a monosaccharide or a polysaccharide. More specifically, the monosaccharide can comprise or consist of a pentose. In particular, the compound can be selected from maltitol, mannitol, sorbitol, lactitol, galactitol, erythritol, arabitol, xylitol and ribitol, preferentially xylitol. This organic film-protective compound can also or alternatively be combined with or replaced by the corresponding saccharide. Particularly, as regards xylitol, it can be combined with or replaced by xylose.

Preferably, the aqueous composition according to the present invention can be characterised in that the organic film-protective and/or hyperosmotic compound is included in a concentration higher than or equal to 5% of mass, preferentially between 10% and 20% of mass relative to the total mass of the composition, particularly a composition of 11% of mass.

According to an embodiment, no chemical preservative has been added to the chemical composition.

The addition of one or more excipients is nonetheless possible, such as aqueous extracts from cosmetic or aromatic plants.

Therapeutic Application

The composition according to the present invention can thus be used as a drug. The composition according to the present can be intended for its use for the prevention or adjuvant treatment of ear, nose and throat (ENT) conditions. The composition can also be intended for the prevention of otitis media.

More specifically, the composition according to the present invention can be intended for its use in the treatment of conditions of the nasal mucous membranes of viral, bacterial or allergic origin, such as sinusitis, rhinitis, nasal polyps, cystic fibrosis, etc.

The composition according to the present invention can also be intended for its use in the prevention of otitis media. Preferably, the aqueous composition according to the present invention can be characterised in that bacterial conditions is due to at least one of the pathogens chosen from the group consisting mainly of *Streptococcus pneumoniae, Haemophilus influenzae, Moraxella catarrhalis* and *Staphylococcus aureus*.

Without wanting to be limited by theory, the inventors have surprisingly found that the composition which is the object of the present invention exhibits synergy among its various beneficial effects, in addition to the individual effects provided by each element, namely:
- deep mechanical cleansing with seawater, which sweeps away viral particles and allergens, protects the epithelium of the nasal cavities and improves motile cilia function,
- a protective effect provided by some seawater ingredients, as described more thoroughly below, and
- a barrier effect against progression of bacteria towards the eustachian tube, provided by the film-protective compound.

The trace elements contained in seawater (such as zinc, copper or magnesium) increase the body's defences against bacterial and viral attacks, and make it possible to reduce the risk of lower respiratory tract infections. Six studies have been conducted to study the effects of zinc supplementation on pneumonia prevention in Bangladesh, India, Peru and South Africa. A total of 5,193 children aged 2 to 59 months old were included. Zinc supplementation is significantly associated with a decrease in the occurrence and prevalence of pneumonia in children aged 2 to 59 months old.

The xylitol/xylose film-protective compound provides a barrier effect against the progression of bacteria towards the eustachian tube, and thus provide protection against otitis media. Maltitol, mannitol, sorbitol, lactitol, galactitol, erythritol, arabitol or ribitol can have effects similar to those of xylitol/xylose.

Administration Device

The object of the present invention relates to a nasal administration device, such as a spray device, characterised in that it comprises a composition according to the present invention.

Any type of nasal administration device can be used. A mechanical pump or aerosol spray device with or without a bag-on-valve can be used, for example. Preferentially, an aerosol spray device with a bag-on-valve is used.

Advantageously, the bag is pressurised, for example at greater than or equal to 1.5 bars, 2 bars, 3 bars, 4 bars, 5 bars or even 10 bars.

Administration devices in the form of aerosol spray devices with a bag-on-valve are designed to reduce and avoid the risk of retro-contamination. This property has been verified by performing the appropriate tests.

EXAMPLES

The examples given below are a mere illustration of the present invention which is not limited to these particular embodiments.

Several compositions were prepared and their osmolarity measured, as shown in Table 1 below.

TABLE 1

| Compositions | A | B | C | D |
| --- | --- | --- | --- | --- |
| Xylitol | 11% | 11% | — | |
| Seawater | 21% | 68% | 30% | 80% |
| Purified water | 68% | 21% | 70% | 20% |
| Mean osmolarity (mosmol/l) | 1100 | 1700 | 300 | 800 |

The quantity of each substance is given as % w/w at 20° C. Mean osmolarity corresponds to the mean of the osmolarities measured for different samples of each composition.

Compositions A and B correspond to embodiments of the present invention. Composition C is an isotonic seawater solution and composition D is a hypertonic seawater solution.

Although it is hypotonic, solution A has an osmolarity that is much higher than that of blood.

Solution B is hypertonic and has an osmolarity that is much higher than that of blood (almost 6 times higher).

Tests were carried out, during which the compositions were administered via nasal spray device to test subjects at differing application dosages.

Composition C has cleansing, purifying and healing effects.

Composition D exerts a nasal decongestion effect.

Composition A is effective in protecting against otitis media in patients. The presence of seawater enables the protective effect to be extended to the entire ENT sphere. Seawater exerts a cleansing, purifying and healing effect on the nasal mucosa.

Composition B combines the beneficial effects of a polyol (ensuring protection against otitis media) with a high seawater concentration. Synergistic effects are multiplied and unexpected. Hyperosmolarity explains the extraordinary decongestant effects found during trials conducted with pilot batches. In fact, a single spray of solution B in each nostril decongested the nose for a relatively long time, depending on the physiological condition of the patient (for one to several hours). There is numerous applications of Solution B. Among these, solution B enables replacing purely chemical decongestants such as corticosteroids or vasoconstrictors, known for their short- or longer-term side effects (tachycardia, arterial hypertension, hormonal imbalance, addiction) in a beneficial and natural way. Unlike purely chemical products, solution B helps improve short- and especially long-term respiratory function by exerting a prophylactic action on ear, nose and throat (ENT) conditions without any side effects. One spray in each nostril before going to bed helps decongest the nose in a lasting way and allows for better sleep thanks to smoother breathing. Its application in reducing snoring and sleep apnoea is perfectly conceivable, with consequent improved lifestyle and an overall decrease in blood pressure, thanks to improved sleep quality.

The invention claimed is:

1. A manufacturing method of an aqueous composition, the method comprising the following steps:
    a) microfiltration of seawater;
    b) addition of purified water;
    c) mixing;
    d) while mixing, addition to the solution from step c) of the organic film-protective and/or hyperosmotic compound;
    e) recovery of the mixture from step d);
    said process being characterized in that the quantity of seawater is higher than or equal to 10% of the total mass of the aqueous composition obtained in step e) and in that the quantity of organic film-protective and/or hyperosmotic compound is higher than or equal to 5% of the total mass of the aqueous composition obtained in step e),
    wherein the composition comprises an organic film-protective and/or hyperosmotic compound comprising a polyol derived from a saccharide compound, the saccharide compound in question or a mixture thereof, and the osmolarity of said composition is higher than 1,000 mosmol/l at 20° C.

2. The manufacturing method according to claim 1, wherein the quantity of seawater is higher than or equal to 15%, 20%, 30%, 40%, 50%, 60%, 70% or 80% of the total mass of the aqueous composition obtained in step e) and/or the quantity of organic film-protective and/or hyperosmotic compound is higher than or equal to 6%, 7%, 8%, 9%, 10%, 15%, or 20% of the total mass of the aqueous composition obtained in step e).

3. An aqueous saline composition comprising an organic film-protective and/or hyperosmotic compound comprising a polyol derived from a saccharide compound, the saccharide compound in question or a mixture thereof, wherein the osmolarity of said composition is higher than 1,000 mosmol/l at 20° C., wherein the polyol derived from a saccharide compound, the saccharide compound in question, or a mixture thereof is selected from maltitol, sorbitol, lactitol, galactitol, erythritol, arabitol, xylitol or ribitol, or a mixture thereof, characterized in that said composition comprises:
    a chloride concentration between 2 and 18 g/kg
    a sodium concentration between 1 and 10 g/kg
    a sulphate concentration between 0.3 and 2.4 g/kg
    a magnesium concentration between 0.1 and 1.2 g/kg
    a calcium concentration between 0.04 and 0.4 g/kg
    a potassium concentration between 0.04 and 0.4 g/kg
    and/or a pH between 4 and 10.

4. An aqueous saline composition comprising an organic film-protective and/or hyperosmotic compound comprising a polyol derived from a saccharide compound, the saccharide compound in question or a mixture thereof, wherein the osmolarity of said composition is higher than 1,000 mosmol/l at 20° C., wherein the polyol derived from a saccharide compound, the saccharide compound in question, or a mixture thereof is selected from maltitol, sorbitol, lactitol, galactitol, erythritol, arabitol, xylitol or ribitol, or a mixture thereof, wherein the composition is in final dosage forms selected from the group consisting of nasal drops, liquid nasal sprays and nasal washes.

5. An aqueous saline composition comprising an organic film-protective and/or hyperosmotic compound comprising a polyol derived from a saccharide compound, the saccharide compound in question or a mixture thereof, wherein the osmolarity of said composition is higher than 1,000 mosmol/l at 20° C., wherein the polyol derived from a saccharide compound, the saccharide compound in question, or a mixture thereof is selected from maltitol, sorbitol, lactitol, galactitol, erythritol, arabitol, xylitol or ribitol, or a mixture thereof, wherein the composition comprises seawater.

6. A nasal administration device, wherein the device includes a spray device, and comprises an aqueous saline composition comprising an organic film-protective and/or hyperosmotic compound comprising a polyol derived from a saccharide compound, the saccharide compound in question or a mixture thereof, wherein the osmolarity of said composition is higher than 1,000 mosmol/l at 20° C., wherein the polyol derived from a saccharide compound, the saccharide compound in question, or a mixture thereof is selected from maltitol, sorbitol, lactitol, galactitol, erythritol, arabitol, xylitol or ribitol, or a mixture thereof.

7. The composition according to claim 3, wherein the osmolarity of said composition is higher than 1,500 mosmol/l at 20° C.

8. The composition according to claim 7, wherein the osmolarity of said composition is less than 2,000 mosmol/l at 20° C.

9. The composition according to claim 3, wherein the pH is between 5 and 9.

10. The composition according to claim 9, wherein the pH is about 7.

11. A method for treating ear, nose and throat (ENT) conditions comprising administering to a patient an aqueous saline composition comprising an organic film-protective and/or hyperosmotic compound comprising a polyol derived from a saccharide compound, the saccharide compound in question or a mixture thereof, wherein the osmolarity of said composition is higher than 1,000 mosmol/l at 20° C., wherein the polyol derived from a saccharide compound, the saccharide compound in question, or a mixture thereof is selected from maltitol, sorbitol, lactitol, galactitol, erythritol, arabitol, xylitol or ribitol, or a mixture thereof.

12. The manufacturing method according to claim 1, wherein the quantity of seawater is higher than or equal to 15%, 20%, 30%, 40%, 50%, 60%, 70% or 80% of the total mass of the aqueous composition obtained in step e) and the quantity of organic film-protective and/or hyperosmotic compound is higher than or equal to 11% of the total mass of the aqueous composition obtained in step e).

13. The composition according to claim 4, wherein the osmolarity of said composition is higher than 1,500 mosmol/l at 20° C.

14. The composition according to claim 13, wherein the osmolarity of said composition is less than 2,000 mosmol/l at 20° C.

15. The composition according to claim 5, wherein the osmolarity of said composition is higher than 1,500 mosmol/l at 20° C.

16. The composition according to claim 15, wherein the osmolarity of said composition is less than 2,000 mosmol/l at 20° C.

17. The nasal administration device according to claim 6, wherein the osmolarity of said composition is higher than 1,500 mosmol/l at 20° C.

18. The nasal administration device according to claim 17, wherein the osmolarity of said composition is less than 2,000 mosmol/l at 20° C.

\* \* \* \* \*